US012575748B2

(12) United States Patent
Kokubo et al.

(10) Patent No.: US 12,575,748 B2
(45) Date of Patent: Mar. 17, 2026

(54) BLOOD PRESSURE-RELATED INFORMATION DISPLAY DEVICE, BLOOD PRESSURE-RELATED INFORMATION DISPLAY METHOD, AND A NON-TRANSITORY COMPUTER-READABLE COMPUTER MEDIUM

(71) Applicants: OMRON HEALTHCARE Co., Ltd., Muko (JP); JICHI MEDICAL UNIVERSITY, Tokyo (JP)

(72) Inventors: Ayako Kokubo, Kyoto (JP); Mitsuo Kuwabara, Kyoto (JP); Shingo Yamashita, Kyoto (JP); Kazuomi Kario, Tochigi (JP)

(73) Assignees: OMRON CORPORATION, Kyoto (JP); JICHI MEDICAL UNIVERSITY, Tokyo (JP)

( * ) Notice: Subject to any disclaimer, the term of this patent is extended or adjusted under 35 U.S.C. 154(b) by 910 days.

(21) Appl. No.: 17/484,790

(22) Filed: Sep. 24, 2021

(65) Prior Publication Data

US 2022/0071495 A1 Mar. 10, 2022

Related U.S. Application Data

(63) Continuation of application No. PCT/JP2020/008980, filed on Mar. 3, 2020.

(30) Foreign Application Priority Data

Mar. 25, 2019 (JP) ................................. 2019-056874

(51) Int. Cl.
*A61B 5/022* (2006.01)
*A61B 5/00* (2006.01)
(Continued)

(52) U.S. Cl.
CPC ............ *A61B 5/022* (2013.01); *A61B 5/4815* (2013.01); *A61B 5/4818* (2013.01);
(Continued)

(58) Field of Classification Search
CPC ..... A61B 5/022; A61B 5/4815; A61B 5/4818; A61B 5/4848; A61B 5/7246; A61B 5/743; G16H 30/00; G16H 40/67; G16H 50/20
See application file for complete search history.

(56) References Cited

U.S. PATENT DOCUMENTS

| | | | | |
|---|---|---|---|---|
| 2014/0194755 | A1* | 7/2014 | Ide | A61B 5/02007 600/494 |
| 2014/0324469 | A1* | 10/2014 | Reiner | G16H 50/70 705/3 |
| 2018/0014791 | A1* | 1/2018 | Montgomery | A61B 5/14551 |

FOREIGN PATENT DOCUMENTS

| | | |
|---|---|---|
| JP | 2006-212218 A | 8/2006 |
| JP | 2015-029565 A | 2/2015 |

(Continued)

OTHER PUBLICATIONS

Jun. 2, 2020 International Search Report issued in International Patent Application No. PCT/JP2020/008980.
(Continued)

*Primary Examiner* — Justin Xu
(74) *Attorney, Agent, or Firm* — OLIFF PLC

(57) ABSTRACT

A blood pressure-related information display device, for visualizing and displaying information relating to blood pressure surges, is provided with: a blood pressure surge detection unit which, from time series data of blood pressure which changes linked to the subject's pulse, detects a blood pressure surge on the basis of a preset determination standard; a bodily state input unit which, together with the time series data of blood pressure, inputs bodily state information
(Continued)

which indicates the bodily state of the subject; an extraction unit which extracts a feature value of the blood pressure surge; a statistical processing unit which performs statistical processing of the extracted feature value of the blood pressure surge; a calculation unit which calculates a feature value of the subject's bodily state; a display processing unit which performs processing for displaying, on a display screen, the correlation between the feature value of the blood pressure surge which was subjected to statistical processing, and the feature value of the bodily state.

4 Claims, 10 Drawing Sheets

(51) Int. Cl.
| | | |
|---|---|---|
| *G16H 30/00* | (2018.01) |
| *G16H 40/67* | (2018.01) |
| *G16H 50/20* | (2018.01) |

(52) U.S. Cl.
CPC .......... *A61B 5/4848* (2013.01); *A61B 5/7246* (2013.01); *A61B 5/743* (2013.01); *G16H 30/00* (2018.01)

(56) References Cited

FOREIGN PATENT DOCUMENTS

| | | | |
|---|---|---|---|
| JP | 2016-064125 | A | 4/2016 |
| JP | 2018-149183 | A | 9/2018 |
| JP | 2018-153232 | A | 10/2018 |
| WO | 2017/082107 | A1 | 5/2017 |
| WO | 2017/179701 | A1 | 10/2017 |
| WO | 2018/168301 | A1 | 9/2018 |
| WO | 2018/168806 | A1 | 9/2018 |

OTHER PUBLICATIONS

Nov. 27, 2020 International Preliminary Report on Patentability issued in International Patent Application No. PCT/JP2020/008980.

* cited by examiner

HOSPITAL TERMINAL

| TIME | AMOUNT OF SURGE | SURGE PEAK VALUE | RISING SURGE RATE | FALLING TIME | ... |
|---|---|---|---|---|---|
| 22:51:05 | 22 | 141 | 0.8 | 9 | ... |
| 23:01:18 | 25 | 143 | 1.1 | 10 | ... |
| 23:25:22 | 27 | 149 | 1.3 | 15 | ... |
| 23:29:10 | 31 | 151 | 2.1 | 21 | ... |
| 23:33:48 | 28 | 153 | 1.8 | 23 | ... |
| ⋮ | ⋮ | ⋮ | ⋮ | ⋮ | ⋮ |

| APNEA START TIME | HYPOPNEA ENDTIME | APNEA TYPE | DURATION [sec] |
|---|---|---|---|
| 23:01:15 | 23:01:38 | OSA | 23 |
| 23:13:22 | 23:13:53 | OSA | 31 |
| 23:14:00 | 23:14:27 | OSA | 27 |
| 23:15:12 | 23:15:47 | CSA | 35 |
| ⋮ | ⋮ | ⋮ | ⋮ |

FIG.9

| EPOC START TIME | SLEEP STAGE | . . . |
|---|---|---|
| 21:00:00 | REM | . . . |
| 21:00:30 | REM | . . . |
| . . . | . . . | . . . |
| 23:50:00 | N1 | . . . |
| 23:50:30 | N1 | . . . |
| ⋮ | ⋮ | ⋮ |

FIG.10

| MEASURING DATE | AHI | AVERAGE OF APNEA DURATION | ··· | AVERAGE OF SURGE FLUCTUATION | AVERAGE OF RISING SURGE RATE | ··· |
|---|---|---|---|---|---|---|
| 2018/7/31 | 26 | 32.5 | ··· | 33.4 | 4.1 | ··· |
| 2018/8/15 | 17 | 20.1 | ··· | 23.3 | 2.9 | ··· |
| 2018/9/2 | 10 | 17.2 | ··· | 20.2 | 2.4 | ··· |
| ⋮ | ⋮ | ⋮ | ⋮ | ⋮ | ⋮ | ⋮ |

| PRESCRIPTION DATE | TYPE OF MEDICATION | NAME OF MEDICATION | DOSAGE | USAGE |
|---|---|---|---|---|
| 2018/8/1 | SLEEPING PILL | MEDICATION A | 50mg | BEFORE SLEEPING |
| 2018/9/3 | SLEEPING PILL | MEDICATION B | 30mg | BEFORE SLEEPING |
| ⋮ | ⋮ | ⋮ | ⋮ | ⋮ |

1

BLOOD PRESSURE-RELATED INFORMATION DISPLAY DEVICE, BLOOD PRESSURE-RELATED INFORMATION DISPLAY METHOD, AND A NON-TRANSITORY COMPUTER-READABLE COMPUTER MEDIUM

CROSS-REFERENCE TO RELATED APPLICATION

This is a continuation application of International Application No. PCT/JP2020/008980, with an International filing date of Mar. 3, 2020, which claims priority of Japanese Patent Application No. 2019-056874 filed on Mar. 25, 2019, the entire content of which is hereby incorporated by reference.

TECHNICAL FIELD

The present invention relates to a blood pressure-related information display device and a blood pressure-related information display method, and more particularly, to a device and method for visualizing and displaying information related to a blood pressure surge of a subject. The present invention also relates to a program for causing a computer to execute such a blood pressure-related information display method.

BACKGROUND ART

It is known that in patients suffering from sleep apnea syndrome (SAS), blood pressure rises sharply at the time of resumption of breathing after apnea and then falls. As used herein, such abrupt blood pressure fluctuations are referred to as "blood pressure surges" (or simply "surges"). Visualizing and displaying information related to the blood pressure surge that has occurred in the patient (for example, the feature value of the blood pressure surge) is considered to be useful for the diagnosis and treatment of SAS.

Conventionally, for example, in FIG. 3 of Patent Document 1 (WO 2017/082107 A1), the amount of surge fluctuation, which is one of the feature values of blood pressure surge in a patient with sleep apnea syndrome (SAS), is displayed as a graph.

SUMMARY OF THE INVENTION

In Patent Document 1, since the frequency of blood pressure surge and the amount of surge fluctuation are visualized, it seems possible to confirm the effect of taking medication by creating this visualization before and after taking the medication.

However, in Patent Document 1, only the index showing the result of the occurrence of the blood pressure surge can be grasped, and it is not possible to grasp how the index causing the blood pressure surge has changed.

It may be possible to confirm the effect of dosing just by grasping the tendency of blood pressure surge such as the frequency of occurrence of blood pressure surge before and after dosing, but if the correlation between the tendency of blood pressure surge and the index causing blood pressure surge, for example, sleep quality, can be visualized and grasped, more effective information can be provided.

Taking sleep quality as an example, it has been confirmed that the tendency of blood pressure surges such as the frequency of occurrence changes depends on the quality of sleep, so hypnotics may be prescribed in actual treatment. An index showing the quality of sleep is the ratio of REM sleep. If the correlation between the frequency of blood pressure surges and the ratio of REM sleep is visualized and clarified, for example, it is possible to judge that the index of blood pressure surge has not changed, although the ratio of REM sleep has been decreased and the quality of sleep has been improved as a result of taking medication. As a result, it is possible to change the type of medication since the factor of blood pressure surge is different from the quality of sleep.

Therefore, an object of the present invention is to provide a blood pressure-related information display device and a blood pressure-related information display method capable of displaying the correlation between the blood pressure surge feature value and the physical condition feature value at the time of detecting the blood pressure surge on the display screen. Another object of the present invention is to provide a program for causing a computer to execute such a blood pressure-related information display method.

To achieve the object, the present invention provides a blood pressure-related information display device that visualizes and displays information related to blood pressure surges, the blood pressure-related information display device comprising:

a blood pressure surge detection unit configured to detect a blood pressure surge based on predetermined determination criteria from time-series data of blood pressure that changes in conjunction with a subject's pulsation;

an input unit configured to input bodily state information indicating a bodily state of the subject, along with the time-series data of the blood pressure;

an extraction unit configured to extract a feature value of the blood pressure surge;

a statistical processing unit configured to perform statistical processing of the extracted feature value of the blood pressure surge;

a calculation unit configured to calculate a feature value of the bodily state of the subject from the input bodily state information; and a display processing unit configured to perform processing for displaying on a display screen, a correlation between the feature value of the blood pressure surge which was subjected to statistical processing, and the feature value of the bodily state.

As used herein, the "predetermined determination criteria" typically refers to criteria for detecting blood pressure surges in patients with sleep apnea syndrome (SAS). For example, as disclosed in Japanese Patent Application No. 2017-048946 and Japanese Patent Application No. 2017-050066, it indicates that both of the time of a surge start point and the time of a surge peak point are included within a peak detection section (for example, a period of 15 beats); the difference (blood pressure fluctuation amount) between a systolic blood pressure value at the time of the surge start point and a systolic blood pressure value at the time of the surge peak point is 20 mmHg (or 15 mmHg) or more; a period between the time of the surge start point and the time of the surge peak point is larger than 5 beats; and a period between the time of the surge peak point and the time of a surge end point is larger than 7 beats.

The "a feature value of the blood pressure surge" includes: a surge fluctuation amount [mmHg] from the start of the blood pressure surge to the peak point of the blood pressure surge; rising a surge rate [mmHg/sec.], or the surge fluctuation amount [mmHg] from the peak point of the blood pressure surge to the end of the blood pressure surge; and a falling surge rate [mmHg/sec.], or a surge area in the rising time or the falling time, or the surge time including the rising time and the falling time, etc. Further, the "a feature value of the blood pressure surge" includes a combination of the above-mentioned feature values by four arithmetic operations.

Further, "bodily state" refers to a sleep stage, such as apnea condition, hypopnea condition, percutaneous arterial blood oxygen saturation, wakefulness, REM sleep, and arousal response state, a heart rate, a pulse rate. The "a feature value of the bodily state" refers to apnea or hypopnea index measured per hour based on the summary data of the apnea or hypopnea, the average value of the apnea or hypopnea duration, or the average value of the reduction amount of the percutaneous arterial oxygen saturation at the time of the occurrence of the blood pressure surge, the average value of the reduction time of percutaneous arterial oxygen saturation, the average value of the bottom value of percutaneous arterial oxygen saturation, the variation average value of a heart rate or a pulse rate, the average value of the peak value of the heart rate or the pulse rate, or a statistical amount of a median or the like. Further, "a feature value of the bodily state" refers to an arousal reaction index, or a proportion of REM sleep and the like.

Further, the "display screen" typically refers to the screen of the display device, but may be, for example, a paper surface output by a printer. The "displaying the correlation" between the feature values of the blood pressure surge and the feature values of the bodily state includes the followings: for example, a plane can be defined by one axis representing the feature value of the blood pressure surge and the other axis representing the feature value of the bodily state. Then, the "displaying the correlation" refers to plotting and displaying points corresponding to the feature value of the blood pressure surge and the feature value of the bodily state on the plane.

In the blood pressure-related information display device of the present disclosure, the blood pressure surge detection unit detects the blood pressure surge based on predetermined determination criteria from the time-series data of the blood pressure that changes in association with the subject's pulsation. The input unit inputs the bodily state information indicating the bodily state of the subject along with the time-series data of the blood pressure. The extraction unit extracts the feature value of the blood pressure surge. The statistical processing unit performs statistical processing of the extracted feature value of the blood pressure surge. The calculation unit calculates the feature value of the bodily state of the subject from the input bodily state information. The display processing unit performs processing on the display screen to display the correlation between the feature value of the blood pressure surge which was subjected to the statistical processing and the feature value of the bodily state. As a result, the user (typically, a medical person such as a doctor or a nurse. The subject may be a user; the same applies hereinafter) can intuitively grasp the correlation between the index showing the result of the fluctuation amount of the blood pressure surge and the index causing the occurrence of the blood pressure surge such as the quality of sleep in the subject by looking at the display screen. This is considered to be useful as a material for evaluating the risk of cardiovascular disease and a material for evaluating the risk of disease of a specific organ in addition to the diagnosis and treatment of SAS.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 9 is a diagram showing an example of measurement summary data for observed apnea/hypopnea events.

FIG. 10 is a diagram showing an example in which the bodily state information at one measurement opportunity is divided for each epoch.

DESCRIPTION OF EMBODIMENT

Hereinafter, embodiments of the present invention will be described in detail with reference to the drawings.
(System configuration)

Figure 1:
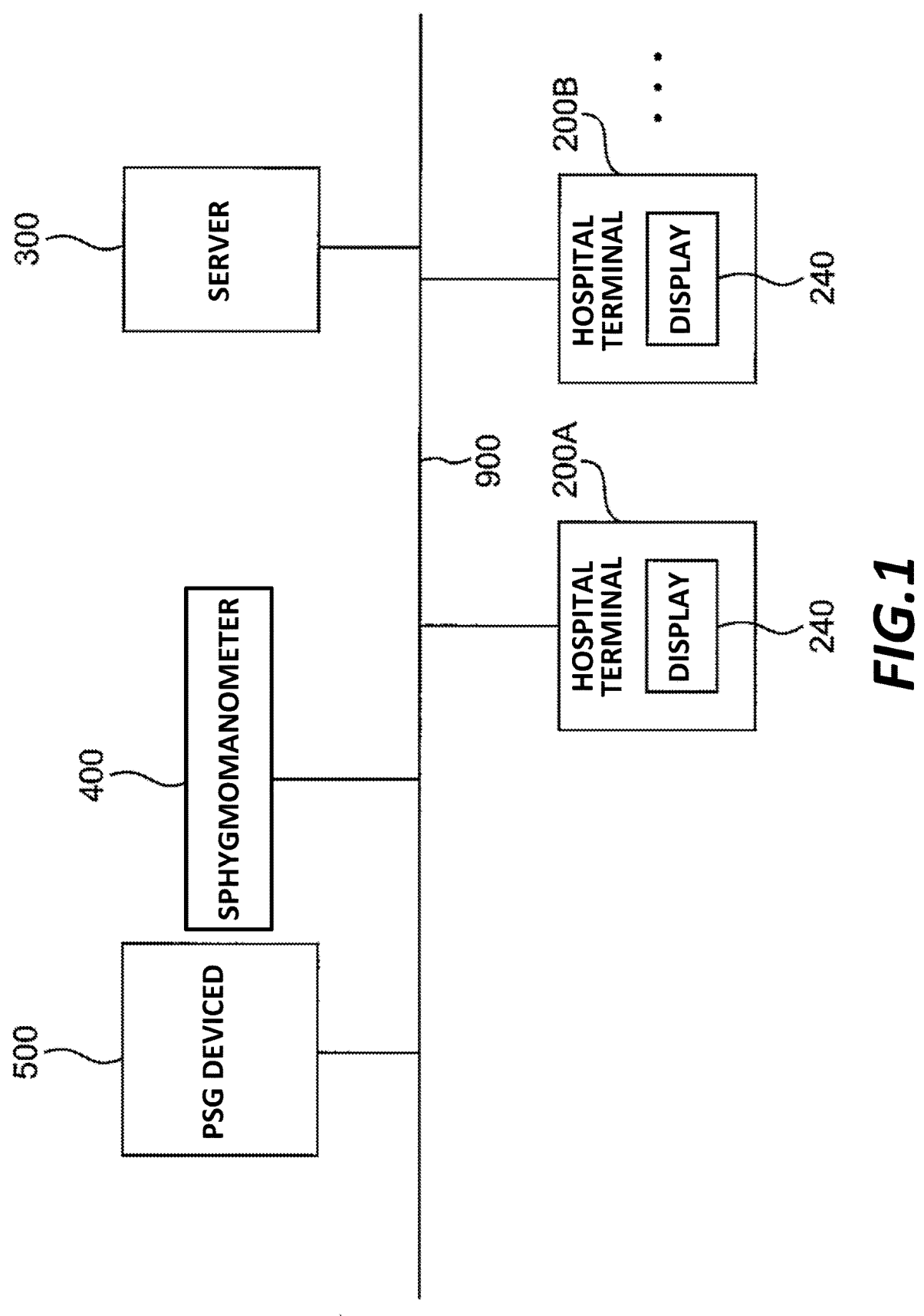
FIG. 1 is a block diagram showing an embodiment in which the blood pressure-related information display device of the present invention is configured as a system on a network.

FIG. 1 shows an example in which the blood pressure-related information display device of the present invention is configured as a system of one embodiment on a network (the whole of the system is indicated by reference numeral 100). The system 100 includes hospital terminals 200A and 200B each having a display 240 as a display screen, a server 300, a tonometry type sphygmomanometer 400, and a PSG (polysomnography) device 500. These hospital terminals 200A and 200B, a server 300, a sphygmomanometer 400, and a PSG device 500 can communicate with each other via a network 900, which is a local area network (LAN) in the hospital. Communication via the network 900 may be either wireless or wired. In this embodiment, the network 900 is an in-hospital LAN (Local Area Network), but is not limited to this, and may be another type of network such as the Internet, or peer-to-peer communication using a USB cable or the like. Although only two hospital terminals 200A and 200B are shown in this example, three or more hospital terminals may be provided.

Figure 2:
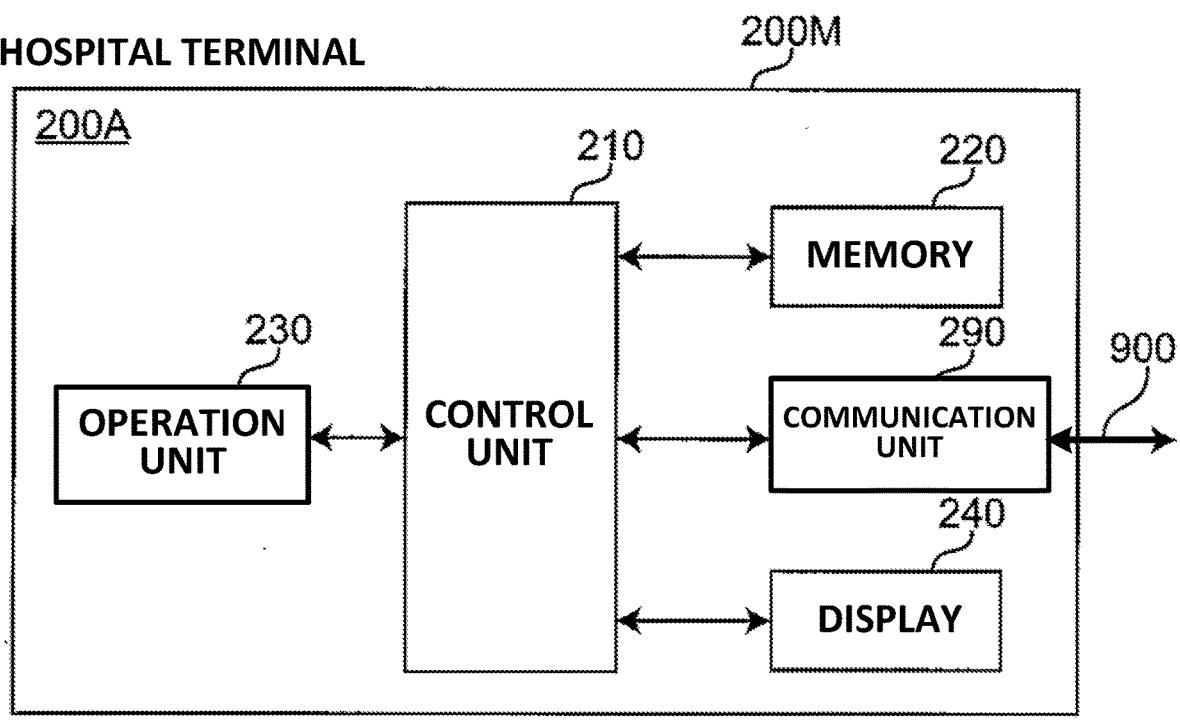
FIG. 2 is a block diagram showing a configuration of a hospital terminal included in the above system.

As shown in FIG. 2, the hospital terminal 200A includes a main body 200M, a control unit 210, a memory 220, an operation unit 230, a display 240 as a display screen, and a communication unit 290 mounted on the main body 200M. The hospital terminal 200A is configured of a commercially available notebook personal computer, in which an application software (computer program) is installed so as to perform the processing described later, and can access to the server 300.

The control unit 210 includes a CPU (Central Processing Unit) and its auxiliary circuits, controls each unit of the hospital terminal 200A, and executes the processing described later according to the programs and data stored in the memory 220. That is, it processes the data input from the operation unit 230 and the communication unit 290. Further, it stores the processed data in the memory 220, displays the data on the display 240, or outputs the data from the communication unit 290.

The memory 220 includes a RAM (Random Access Memory) used as a work area required for the control unit 210 to execute a program, and a ROM (Read Only Memory) for storing a basic program for execution by the control unit 210. Further, a semiconductor memory (memory card, SSD (Solid State Drive)) or the like may be used as a storage medium of an auxiliary storage device for assisting the storage area of the memory 220.

In this example, the operation unit 230 is composed of a keyboard and a mouse, and typically inputs an operation signal indicating an operation by a doctor as a user to the control unit 210. Further, the operation unit 230 may be composed of other operation devices such as a touch panel in place of or in addition to the keyboard and mouse.

The display 240 includes a display screen (for example, an LCD (Liquid Crystal Display) or an EL (Electroluminescence) display). The display 240 is controlled by the control unit 210 to display a predetermined image on the display screen.

The communication unit 290 transmits the information from the control unit 210 to the server 300 via the network 900.

Although not shown for simplicity, the other hospital terminals 200B, . . . have the same configuration as the hospital terminal 200A.

Figure 3:
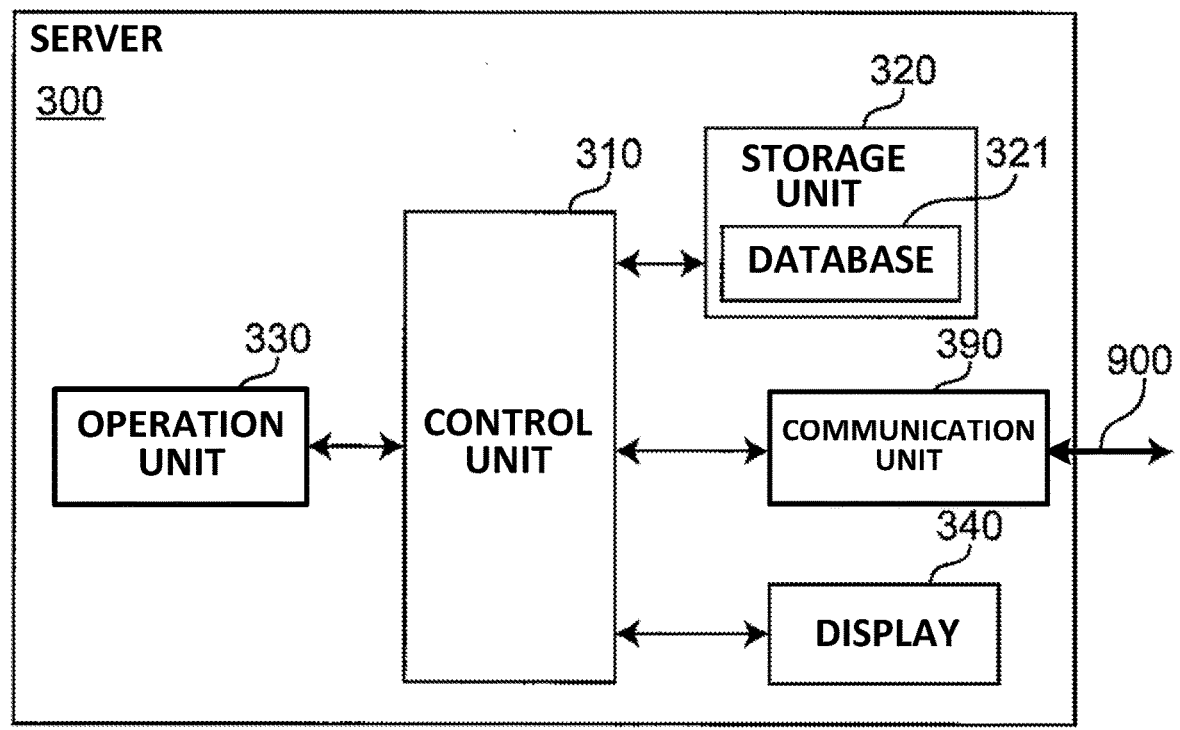
FIG. 3 is a block diagram showing a configuration of a server included in the above system.

As shown in FIG. 3, the server 300 includes a control unit 310, a storage unit 320, an operation unit 330, a display 340, and a communication unit 390. The server 300 is a general-purpose computer device in which a program (software) is installed so as to perform a process described later.

The control unit 310 includes a CPU and its auxiliary circuits, controls each unit of the server 300, executes a predetermined process according to the programs and data stored in the storage unit 320, and processes the data input from the operation unit 330 and the communication unit 390. Further, it stores the processed data in the storage unit 320, displays the data on the display 340, or outputs the data from the communication unit 390.

The storage unit 320 includes a RAM used as a work area required for the control unit 310 to execute a program, and a ROM for storing a basic program for execution by the control unit 310. The storage unit 320 is provided database 321 containing blood pressure measurement data sent from many subjects. Further, as a storage medium of an auxiliary storage device for assisting the storage area of the storage unit 320, a magnetic disk (HD (Hard Disk), FD (Flexible Disk)), an optical disk (CD (Compact Disc), DVD (Digital Versatile Disk), BD (Blu-ray Disc (registered trademark))), an optical magnetic disk (MO (Magneto-Optical disk)), a semiconductor memory (memory card, SSD), or the like may be used.

In this example, the operation unit 330 is composed of a keyboard and a mouse, and inputs an operation signal indicating an operation by the user to the control unit 310. Further, the operation unit 330 may be composed of other operation devices such as a touch panel in place of or in addition to the keyboard and mouse.

The display 340 includes a display screen (for example, an LCD or an EL display). The display 340 is controlled by the control unit 310 to display a predetermined image on the display screen.

The communication unit 390 transmits the information from the control unit 310 to another device (hospital terminal 200A in this example) via the network 900, and receives the information transmitted from the other devices via the network 900 to deliver it to the control unit 310.

Figure 4:
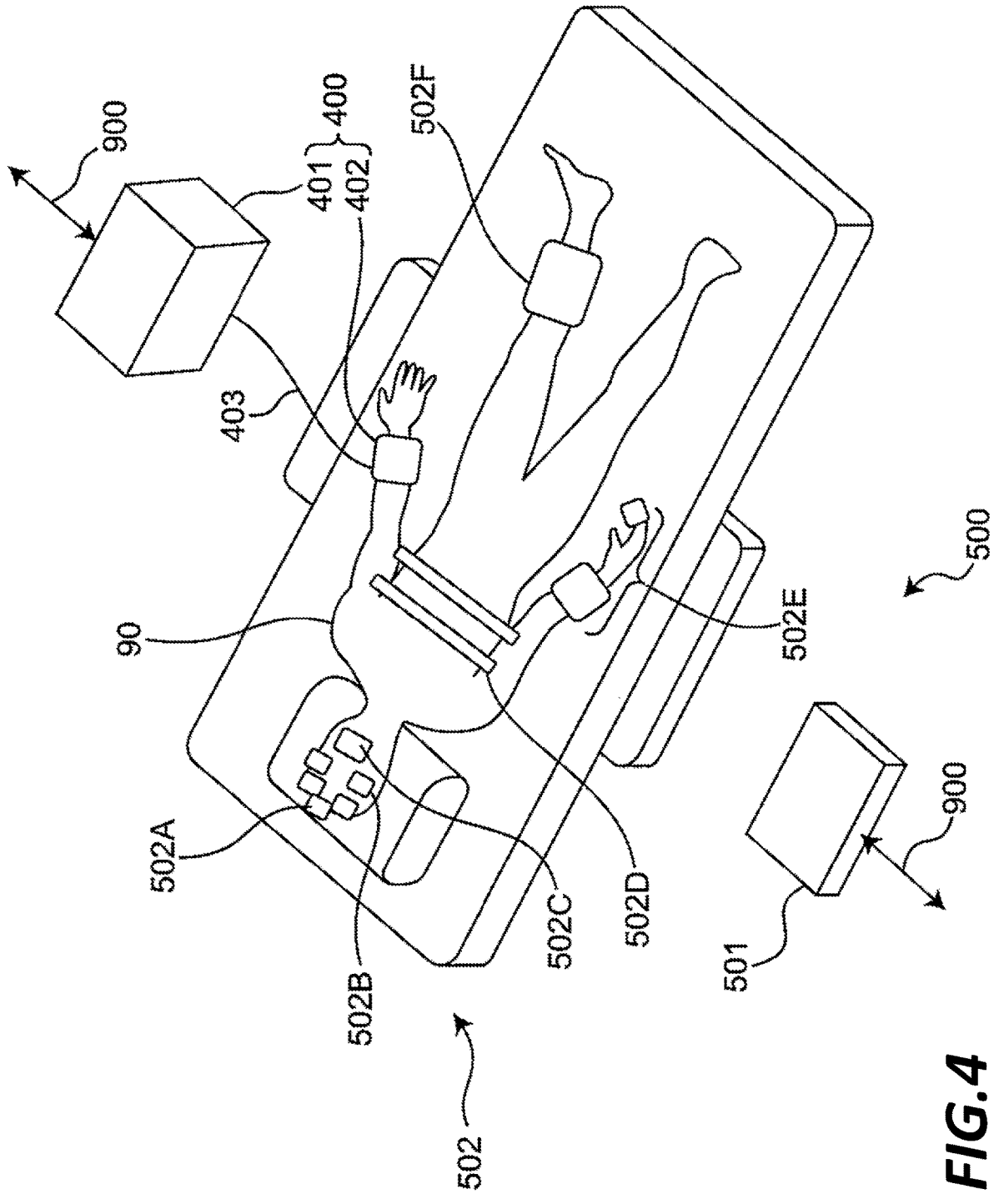
FIG. 4 is a diagram showing an aspect of measuring the time-series data of a subject's overnight blood pressure and a bodily state that may cause a blood pressure surge by the above system.

In this example, the sphygmomanometer 400 shown in FIG. 1 is composed of a tonometry type sphygmomanometer as disclosed in Japanese Patent Application No. 2017-050066. As shown in FIG. 4, the sphygmomanometer 400 is provided with: a pressure sensor unit 402 that continuously detects a pressure pulse wave of a radial artery passing through a measurement site (for example, a left wrist of a subject 90) by a tonometry method for each beat; and a main unit 401 that outputs a change in pressure detected by the pressure sensor unit 402 as time-series data of blood pressure. The pressure sensor unit 402 and the main unit 401 are connected by a signal cable 403. The tonometry method is a method for determining blood pressure by measuring a pressure pulse wave by compressing a blood vessel with a pressure sensor unit 402 (for example, a pressure pulse wave sensor). Assuming that the blood vessel is a circular tube with a uniform thickness, the relational expression between the internal pressure (blood pressure) of the blood vessel and the external pressure of the blood vessel (the pressure of the pressure pulse wave) can be derived according to the Laplace's law, considering a blood vessel wall regardless of a blood flow in the blood vessel and the presence or absence of pulsation. Under the condition that the blood vessel is compressed on a pressing surface by this relational expression, the pressure of the pressure pulse wave and the blood pressure can be approximated to be equal by approximating the radii of an outer wall and an inner wall of the blood vessel. Therefore, after that, the pressure of the pressure pulse wave becomes the same value as the blood pressure. As a result, the sphygmomanometer 400 outputs time series data 801 of the blood pressure associated with measurement time (time) and the blood pressure by measuring a blood pressure value of the measurement site (for example, the left wrist) for each heartbeat, in the manner shown in FIG. 6A, for example. Overnight time series data 801 includes beat-corresponding peaks (peaks corresponding to systolic blood pressure (SBP) or diastolic blood pressure (DBP)) for about 30,000 beats.

Further, the PSG device 500 shown in FIG. 1 is composed of a commercially available PSG device (for example, Neurofax (registered trademark) EEG-9200 manufactured by Nihon Kohden Co., Ltd.) in this example. As shown in FIG. 4, the PSG device 500 includes a sensor group 502 and a main unit 501 that processes signals from the sensor group

502 to output information that identifies the physical condition of the subject 90. In this example, the sensor group 502 includes: an electroencephalogram detection electrode 502A for detecting an electroencephalogram; an eye movement detection electrode 502B for detecting eye movement; an air flow sensor 502C for detecting an airflow associated with breathing; an electrocardiogram electrode 502D for obtaining an electrocardiogram; a pulse oximeter 502E for detecting percutaneous electroencephalographic oxygen saturation ($SpO_2$); and an electromyogram electrode 502F for obtaining an electromyogram. The sensor group 502 and the main unit 501 are connected by a signal cable (not shown) via a cable box (not shown). In this example, the PSG device 500 can output information representing an apnea period (or hypopnea period), a sleep stage (wakefulness, REM sleep, non-REM sleep), arousal response and/or a period in which $SpO_2$ is low (these are collectively referred to as a "bodily state specifying period"), as bodily state information of the subject 90. Here, "apnea" during sleep means "a state in which breathing stops for 10 seconds or more". Further, "hypopnea" means that the ventilation by respiration is reduced to 50% or less for 10 seconds or more. Further, "REM sleep" refers to sleep accompanied by rapid eye movement, "non-REM sleep" refers to sleep not accompanied by rapid eye movement, and "wakefulness" refers to a state of being awake. $SpO_2$ refers to a value measured (percutaneously) through a skin as to what percentage of hemoglobin contained in red blood cells flowing in arterial blood is bound to oxygen. The "period in which $SpO_2$ is "low" refers to the period in which $SpO_2$ is less than 90% in this example. Arousal response refers to a momentary change during sleep to indicate wakefulness.

Figure 6A:
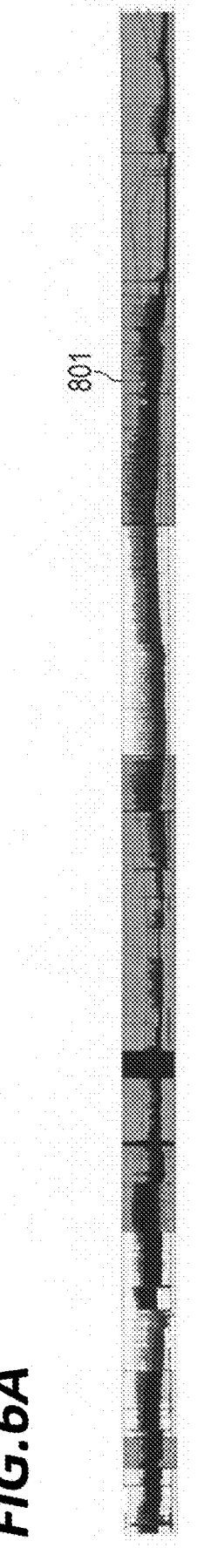
FIG. 6A is a diagram showing the time-series data of the overnight blood pressure of the subject.
Figure 6B:
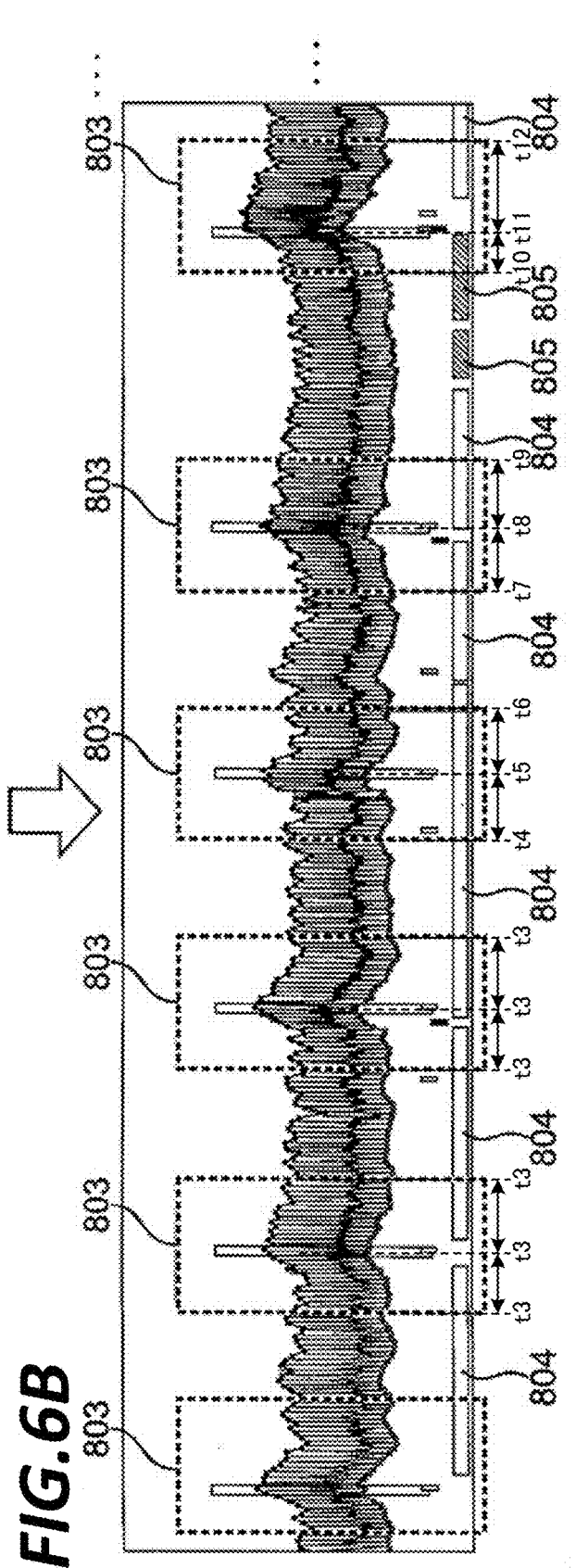
FIG. 6B is an enlarged view of a part of FIG. 6A to show the blood pressure surge detected on the time-series data and the apnea/hypopnea event measured by the PSG device.
Figure 6B:
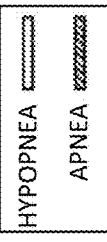
Figure 6B:

For example, in FIG. 6B, which is an enlarged view of a part of FIG. 6A, the "apnea" period is indicated by shaded bars 805, 805, . . . . Also, the "hypopnea" period is indicated by the white bars 804, 804, . . . . In such an embodiment, the PSG device 500 can output a plurality of types of information representing a bodily state specifying period for the subject 90.

(Blood Pressure Related Information Display Method)

This system 100 creates image data on the server 300 and displays the image data on a hospital terminal (for example, 200A). For the creation and display of the image data, by using the time-series data of the blood pressure in which the measurement time (time) output by the sphygmomanometer 400 and the blood pressure are associated with each other, and the information indicating the bodily state specifying period output by the PSG device 500, the image data is created and displayed as follows.

(Creation of Image Data on Server 300)

i) In the present embodiment, in the embodiment shown in FIG. 4, the subject 90 is continuously measured for blood pressure using the sphygmomanometer 400 and for the bodily state using the PSG device 500 overnight (including the sleep period). This is used as one measurement opportunity. Then, after the subject 90 is examined and dosed, measurement opportunities are provided a plurality of times, statistical processing is performed on the measurement data for each measurement opportunity, and the results for each measurement opportunity are plotted on a graph to create and display the image data.

At each measurement opportunity, the time-series data of blood pressure from the sphygmomanometer 400 and the information indicating the bodily state specifying period from the PSG device 500 are received by the hospital terminal 200A and temporarily stored in the memory 220.

Figure 5:
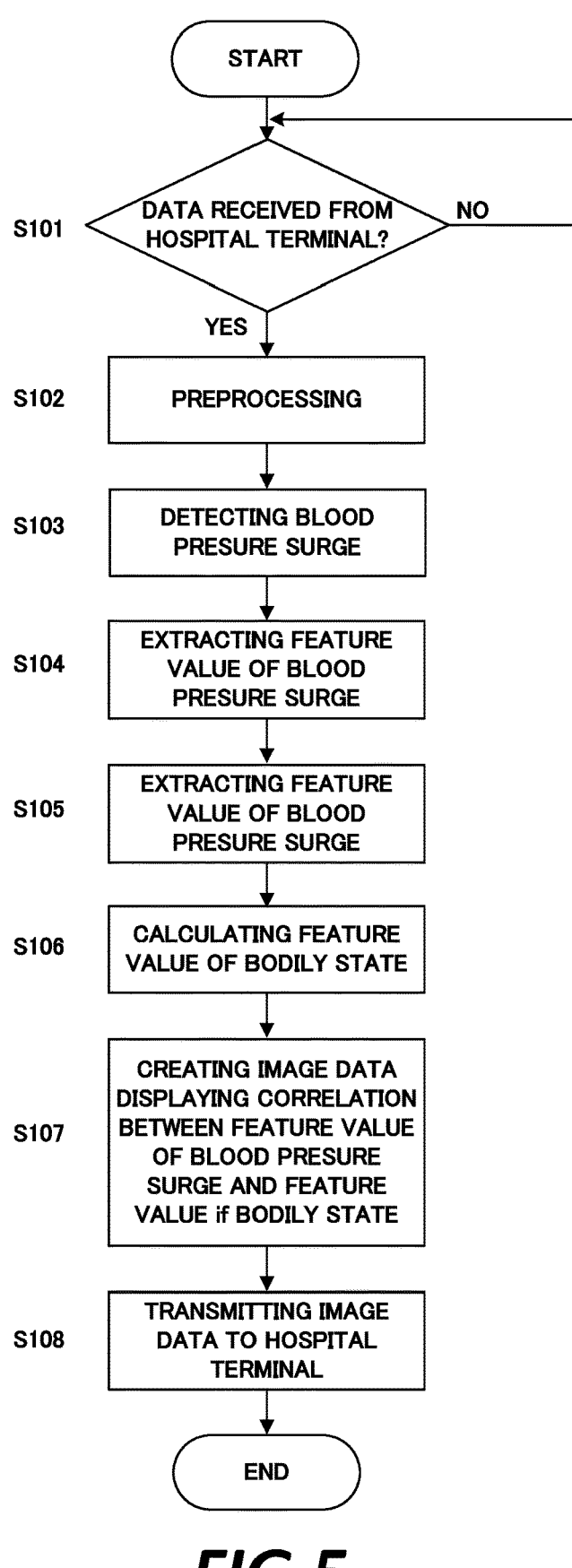
FIG. 5 is a diagram showing an operation flow of the above server when executing a blood pressure-related information display method.

Subsequently, for example, a doctor as a user operates the operation unit 230 of the hospital terminal 200A to transmit the time-series data of the blood pressure measured for the subject 90 and the information indicating the bodily state specifying period, which are combined with each other, to the server 300 via the network 900.

ii) FIG. 5 is a flowchart showing the operation of the server 300. In this example, the server 300 is always in an operating state (however, the maintenance period and the like are excluded), and the control unit 310 of the server 300 determines whether or not there is data received from the hospital terminal 200A at predetermined intervals (FIG. 5: S101). When the control unit 310 of the server 300 determines that the above-mentioned time-series data of blood pressure and information representing the bodily state specifying period have been received from the hospital terminal 200A via the network 900 and the communication unit 390 (FIG. 5: S101; YES), it stores the received time-series data of the blood pressure and the information representing the bodily state specifying period in the database 321 of the storage unit 320. In this case, the control unit 310 and the communication unit 390 function as a bodily state input unit. Then, the control unit 310 executes the processes of steps S102 to S107 described below.

iii) First, the control unit 310 performs preprocessing such as smoothing and noise removal using a known moving average or the like with respect to the time series data of blood pressure, and high frequency component removal using a low-pass filter, or the like (FIG. 5: S102).

iv) Next, the control unit 310 functions as a blood pressure surge detection unit, and detects blood pressure surges based on predetermined determination criteria from the time-series data of the blood pressure of the subject 90, for example, as disclosed in Japanese Patent Application No. 2017-0489946 and Japanese Patent Application No. 2017-050066 (FIG. 5: S103). As a result, for example, in FIG. 6B as shown by the broken line rectangular frames 803, 803, . . . , a plurality of blood pressure surges are detected. It is said that hundreds of blood pressure surges can occur overnight. In this example, peaks corresponding to systolic blood pressure (SBP) are plotted (in FIG. 6B, for example, one of the peaks corresponding to SBP is shown as P10), and they are connected by an envelope. In addition, peaks corresponding to diastolic blood pressure (DBP) are plotted (in FIG. 6B, one of the peaks corresponding to DBP is shown as P11 for example), and they are connected by an envelope.

Figures 7, 8:
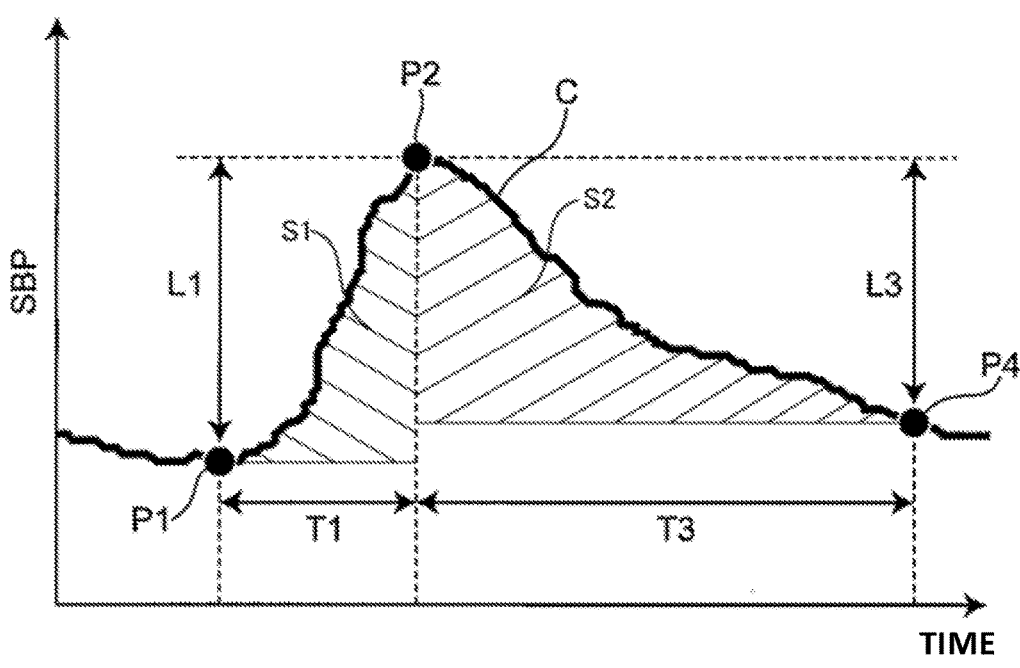
FIG. 7 is a diagram illustrating a blood pressure surge waveform (individual waveform) and explaining determination criteria for detecting a blood pressure surge and a feature value.
FIG. 8 is a diagram showing a feature value of the blood pressure surge calculated at one measurement opportunity.

FIG. 7 shows an example of an individual waveform of a blood pressure surge with a curve C. The "predetermined determination criteria" for detecting the blood pressure surge in the present embodiment refers to the following criteria.

(a) As shown in FIG. 7, the time from the surge start point P1 to the time of the surge peak point P2 are included in a peak detection section (for example, a period of 15 beats), and the difference (blood pressure fluctuation amount) L1 between the systolic blood pressure value (SBP) at the time of the surge start point P1 and the systolic blood pressure value (SBP) at the time of the peak point P2 is 20 mmHg (or 15 mmHg) or more.

(b) A period T1 between the time of the surge start point P1 and the time of the peak point P2 is larger than 5 beats, and a period T3 between the time of the peak point P2 and the time of the surge end point P4 is greater than 7 beats.

In the example shown in FIG. 7, the surge start point P1 is defined as a point that gives a minimum value of the systolic blood pressure value (SBP) before the peak point P2. The surge end point P4 is defined as a point where the blood pressure drops by $L1 \times 0.75$ ($=L3$) from the peak point P2 after the peak point P2.

v) Next, the control unit 310 functions as an extraction unit to extract the feature value of the detected blood pressure surge. The peak point P2, the surge start point P1 and the surge end point P4 shown in FIG. 7 correspond to the feature value of the blood pressure surge. In the example shown in FIGS. 7, L1, L3, T1, and T3 can be used as the feature value of the surge. T1 is the difference between the time at the peak point P2 and the time at the surge start point P1, and is referred to as a rising time. T3 is the difference between the time at the peak point P2 and the time at the surge end point P4, and is referred to as a falling time. L1 is the difference between the blood pressure value at the peak point P2 and the blood pressure value at the surge start point P1, and is referred to as a surge fluctuation amount during the rise time. L2 is the difference between the blood pressure value at the peak point P2 of the blood pressure surge and the blood pressure value at the surge end point P4, and is referred to as a surge fluctuation value during the falling time. Further, the surge area S1 or S2 shown by the diagonal line in FIG. 7 may be used as a feature value of the blood pressure surge. Further, a surge time obtained by adding the rising time T1 and the falling time T3 may be used as a feature value of the blood pressure surge. Further, the rising surge rate obtained by dividing the surge fluctuation amount L1 in the rising time by the rising time, or the falling surge rate obtained by dividing the surge fluctuation amount L3 in the falling time by the falling time may be used as a feature value of the blood pressure surge. Further, a combination of the above-mentioned feature values of blood pressure surge by four arithmetic operations may be used as a feature value of the blood pressure surge. The above-mentioned feature values correspond to the specific feature value shown in FIG. 8.

In the present embodiment, as an example, the control unit 310 extracts the surge fluctuation amount L1 at the rise time T1 as a feature value of the blood pressure surge for each blood pressure surge.

vi) Next, the control unit 310 functions as a statistical processing unit to perform statistical processing of the feature value of the blood pressure surge (FIG. 5: S105). Examples of the statistical processing include a process of calculating the average of a plurality of the feature values of the blood pressure surges extracted for each measurement opportunity, standard deviation, maximum value, minimum value, quartile, and the like.

As an example, an example of calculating the average of the surge fluctuation amount will be described with reference to FIG. 6B. In FIG. 6B, the peak point P2 is detected at time t2, t5, t8, t11, t14, and t17. In FIG. 6B, the peak point P2 is included inside the solid rectangle. Further, the surge start point P1 is detected at times t1, t4, t7, t10, t13, and t16.

In this case, the control unit 310 first calculates the surge fluctuation amounts (1) to (6) for each of the first to sixth rising times. For example, it is assumed that surge fluctuation amount $(1)=L1-1$, surge fluctuation amount $(2)=L1-2$, surge fluctuation amount $(3)=L1-3$, surge fluctuation amount $(4)=L1-4$, surge fluctuation amount $(5)=L1-5$ and the surge fluctuation amount $(6)=L1-6$.

Then, the average of the surge fluctuation amounts (1) to (6) is calculated as $\{(L1-1)+(L1-2)+(L1-3)+(L1-4)+(L1-5)+(L1-6)\}/6$.

In this way, the control unit 310 calculates n surge fluctuation amounts at one measurement opportunity, and divides the total from the surge fluctuation amount (1) to the surge fluctuation amount (n) by n pieces to calculate the average amount of surge fluctuation in one measurement opportunity. Further, the control unit 310 stores the calculated average of the surge fluctuation amounts in the storage unit 320.

Note that the average surge fluctuation amount may be calculated every hour and stored in the storage unit 320, and then the average surge fluctuation amount at one measurement opportunity may be calculated. Further, not only the average of the surge fluctuation amount but also the average of the rising surge rate and the average of the falling time may be calculated together.

vii) Next, the control unit 310 functions as a calculation unit to calculate the feature value of the bodily state based on the information representing the bodily state specifying period (Fit. 5: S106). Information representing the bodily state specifying period of the subject 90 includes an apnea period, a hypopnea period, a REM sleep period, a non-REM sleep period, an arousal period, a period in which $SpO_2$ is low, and the like.

In the present embodiment, as an example, the control unit 310 uses AHI (Apnea Hypopnea Index), which is the total number of apnea periods and hypopnea periods per hour of sleep, as a feature value of the bodily state.

The PSG device 500 transmits, for example, measurement summary data for the observed apnea/hypopnea events to the server 300, as shown in FIG. 9. The control unit 310 stores the measurement summary data transmitted from the PSG device 500 in the storage unit 320.

In FIG. 9, OSA refers to obstructive sleep apnea, which is characterized by apnea (stopping airflow) and hypopnea (reducing airflow) due to repeated upper airway collapse during sleep. CSA is central sleep apnea, referring to a condition in which the lack of respiratory drive during sleep causes repetitive ventilatory insufficiency, and gas exchange is impaired.

The control unit 310 calculates the AHI, which is the total number of apnea periods and hypopnea periods per hour of sleep in one measurement opportunity, based on the measurement summary data as shown in FIG. 9.

As shown in FIG. 10, the measurement summary data transmitted from the PSG device 500 may be data in which the bodily state information in one measurement opportunity is divided for each epoch (for example, every 30 seconds). The data shown in FIG. 10 includes sleep stage information. In FIG. 9, REM represents REM sleep and N1 represents stage 1 of non-REM sleep. When the measurement summary data transmitted from the PSG device 500 is such data, the control unit 310 may calculate the ratio of REM sleep as a feature value of the bodily state.

In addition to the above-mentioned feature values, the feature value of the bodily state include the average value of the duration of apnea/hypopnea, the average value of the amount of decrease in $SpO_2$, the average value of the bottom value of $SpO_2$, the arousal response index, the average value of the fluctuation amount of the heart rate, the average value or the median value of the peak values of the heart rate, and the like. Further, although it is assumed that the PSG device 500 is used in this embodiment, it is not always necessary to use the PSG device 500. When the PSG device 500 is not used, the instantaneous pulse rate for each beat calculated in the tonometry type sphygmomanometer may be used, and the average value of the fluctuation amount of the pulse rate, the average value or median value of the peak value of the pulse rate using the instantaneous pulse rate may be used as a feature value of the bodily state.

Figures 11, 12:
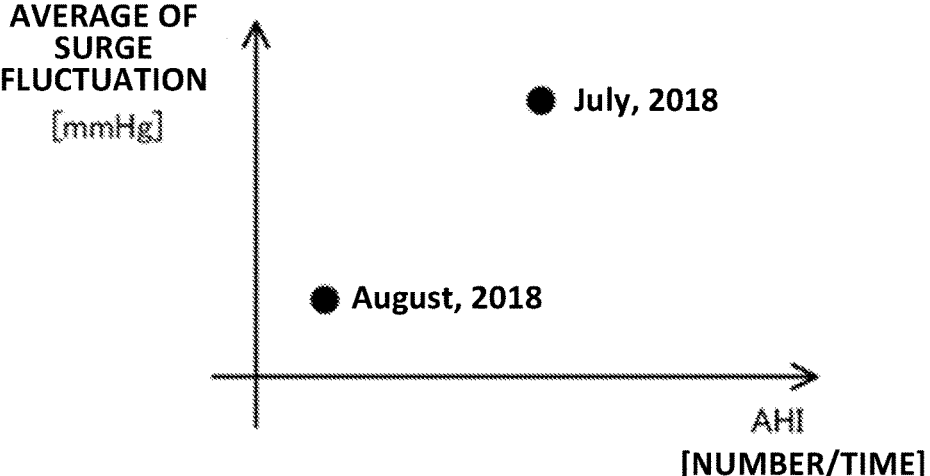
FIG. 11 is a diagram showing an example of statistic of the feature value of the blood pressure surge and the data of the bodily state at each measurement opportunity.
FIG. 12 is a diagram showing an example of an image displaying the correlation between the feature value of the blood pressure surge and the feature value of the bodily state displayed on the display screen of a hospital terminal.

The control unit 301 stores the statistical amount of the feature value of the blood pressure surge and the feature value of the bodily state, which are calculated as described above, in the storage device 320 for each measurement opportunity. FIG. 11 shows an example in which the feature values of the three measurement opportunities of Jul. 31, 2018, Aug. 15, 2018, and Sep. 2, 2018 are stored in the storage device 320.

viii) Next, the control unit 310 functions as a part of the display processing unit to create image data for displaying the correlation between the feature value of the blood pressure surge and the feature value of the bodily state for each measurement opportunity (FIG. 5: S107). Then, the control unit 310 transmits image data to the hospital terminal 200A or the hospital terminal 200B via the network 900 and the communication unit 390 (FIG. 5: S108).

FIG. 12 shows an example of an image showing the correlation between the feature value of the blood pressure surge displayed on the display 240 of the hospital terminal 200A or the hospital terminal 200B and the feature value of the bodily state. As shown in FIG. 12, the control unit 310 sets the coordinate system defined by one axis representing the feature value of the blood pressure surge (vertical axis in the example shown in FIG. 12) and the other axis representing the feature value of the bodily state (horizontal axis in the example shown in FIG. 12). Then, it performs the processing for displaying the correlation as an image in which the points corresponding to the feature value of the blood pressure surge and the feature value of the bodily state are plotted.

Further, the control unit 310 may associate the medication information with each of the above-mentioned feature values when creating the image data.

Figures 13, 14:
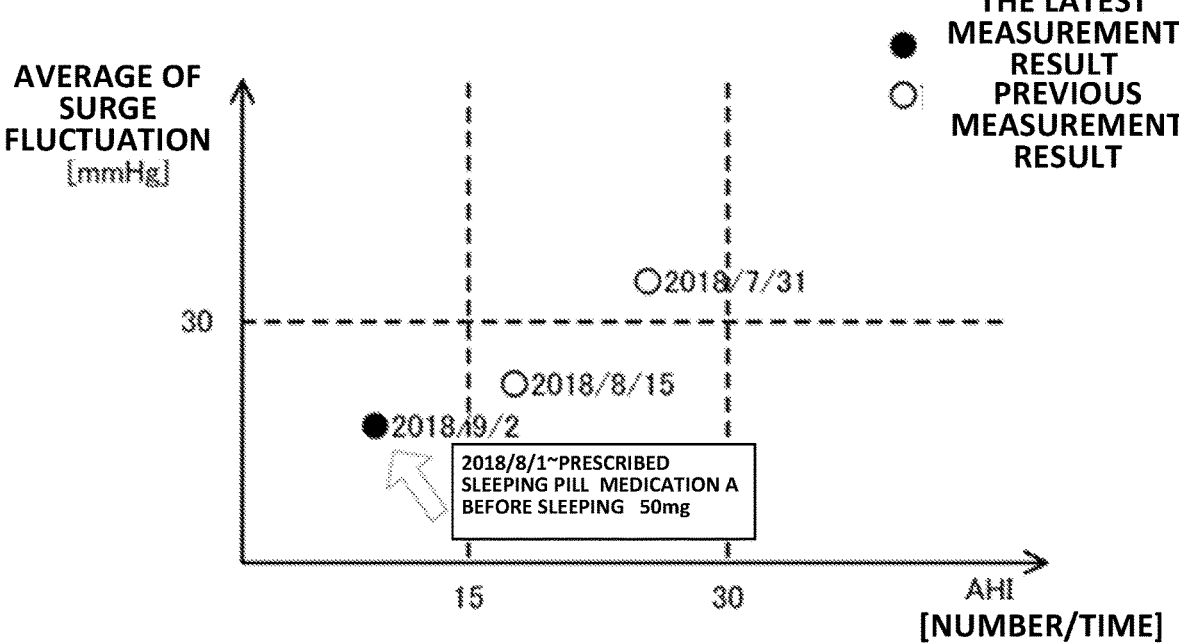
FIG. 13 is a diagram showing an example of medication information.
FIG. 14 is a diagram showing an example of an image in which the medication information is associated as a parameter with the correlation between the feature value of the blood pressure surge displayed on the display screen of the hospital terminal and the feature value of the bodily state.

When the medication information is associated with each of the above-mentioned feature values, the control unit 310 of the server 300 functions as a medication information input unit to input the medication information from the hospital terminal 200A or the hospital terminal 200B. FIG. 13 is a diagram showing an example of medication information. In the example shown in FIG. 13, medication information that 50 mg of a medication A was prescribed as a hypnotic on Aug. 1, 2018 and 30 mg of a mediation B was prescribed as a hypnotic on Sep. 3, 2018 was sent to the server 300. The control unit 310 functions as a medication information input unit to input the medication information, create image data, and transmit the image terminal 200A or the hospital data to the hospital terminal 200B.

FIG. 14 shows an example of an image displaying the medication information in association with the correlation between the feature value of the blood pressure surge displayed on the display 240 of the hospital terminal 200A or the hospital terminal 200B and the feature value of the bodily state.

In the example shown in FIG. 14, measurement opportunities are provided three times on Jul. 31, 2018, Aug. 15, 2018, and Sep. 2, 2018, and the image is viewed on Sep. 3, 2018.

The measurement result on Sep. 2, 2018, which is the latest measurement result, is indicated by a black circle, and the measurement results before that are indicated by a white circle. Further, the measurement result on Sep. 2, 2018, which is the latest measurement result, is displayed so that the measurement result is associated with the medication information prescribed on Aug. 1, 2018 as a parameter.

The white arrows in FIG. 14 are images of mouse cursors when hospital terminals 200A and 200B are realized by a personal computer. When the user mouses over the plotted points, the medication information prescribed at the most recent visit is displayed. Here, it means that "this value was observed as a result of the previous medication".

In this example, as a result of dosing of the sleeping pill A, the value of AHI, which is an index causing blood pressure surge, and the feature value of the blood pressure surge, which is an index of the resulting blood pressure surge, are both improved.

As in the example shown in FIG. 14, on the image showing the correlation between AHI, which is an index causing blood pressure surge, and the feature value of the blood pressure surge, which is an index of the blood pressure surge generated as a result, AHI and a value that serves as a reference for the feature value of the surge may be displayed as an auxiliary line shown by a dotted line in FIG. 14.

Further, in FIG. 14, the first measurement result on Jul. 31, 2018 may be plotted with a marker to be displayed separately from the second and third measurement results.

As described above, according to the present embodiment, it is possible to display the correlation between the feature value of the blood pressure surge and the feature value of the bodily state at the time of detecting the blood pressure surge on the display screens of the hospital terminals 200A and 200B.

Therefore, the user can grasp the correlation between the index showing the result such as the fluctuation amount of the blood pressure surge in the subject and the index causing the occurrence of the blood pressure surge such as the quality of sleep, more intuitively. This is considered to be useful as a material for evaluating the risk of cardiovascular disease and a material for evaluating the risk of disease of a specific organ, in addition to the diagnosis and treatment of SAS.

Further, according to the present embodiment, when the medication information is displayed in association with the above correlation, it becomes easier for the user to grasp the relationship among an index showing the result regarding the occurrence of the blood pressure surge, an index causing the occurrence of the blood pressure surge, and the medication. Therefore, the user can easily grasp whether or not there is a change in the index showing the result regarding the occurrence of the blood pressure surge before and after the dosing and the index causing the occurrence of the blood pressure surge.

Modification Example 1

In the above-described embodiment, the server 300 creates image data representing the correlation, and the display 240 of the hospital terminals 200A, 200B, . . . displays the image, but the present invention is not limited to this. The control unit 310 of the server 300 transmits only the data for image creation instead of transmitting the image data representing the correlation to the hospital terminals 200A, 200B, . . . and the control unit 210 of the hospital terminals 200A, 200B, . . . may exclusively create the image data representing the correlation.

Modification Example 2

Further, in the above-described embodiment, the blood pressure-related information display device of the present invention is configured as a system 100 on a network including the hospital terminals 200A, 200B, . . . and the server 300, but the present invention is not limited thereto.

For example, the blood pressure-related information display device of the present invention may be configured with only one of the hospital terminals 200A, 200B, That is, the hospital terminal (for example, 200A) may execute all of the above-mentioned blood pressure-related information display methods (including the reception of the time-series data of the blood pressure from the sphygmomanometer 400, the reception of information indicating the bodily state specifying period from the PSG device 500, and the display of image data Im etc., on the display screen of the display 240).

In that case, in the memory 220 of the hospital terminal 200A, a program for causing the control unit 210 to execute the above-mentioned blood pressure-related information display method is installed. Thereby, the blood pressure-related information display device of the present invention can be configured in a small size and compactly.

In addition, the above-mentioned blood pressure-related information display method can be recorded on CD (compact disc), DVD (digital universal disc), and non-transitory data such as a flash memory, as software (computer program). By installing the software recorded on such a recording medium on a substantial computer device such as a personal computer, a PDA (Personal Digital Assistance), or a smartphone, the above-mentioned blood pressure-related information display method can be executed by those computer devices.

Modification Example 3

Further, in the above-described embodiment, the sphygmomanometer 400 is a tonometry type sphygmomanometer, but the present invention is not limited to this. The sphygmomanometer 400 may include a light emitting element that irradiates light toward an artery passing through a corresponding portion of the measurement site and a light receiving element that receives reflected light (or transmitted light) of the light, to continuously detect the blood pressure by detecting a pulse wave of an artery as the change of the volume (photoelectric method). Further, the sphygmomanometer 400 may be provided with a piezoelectric sensor that is in contact with the measurement part, to detect the strain due to the pressure of the artery passing through the corresponding part of the measurement part as a change in electrical resistance, and to detect continuously the blood pressure based on the changes in this electrical resistance (piezoelectric method). Further, the blood pressure monitor 400 may include a transmitting element that sends a radio wave (transmitted wave) toward an artery passing through a corresponding portion of the measured site, and a receiving element that receives a reflected wave of the radio wave, to detect the change in the distance between the artery and the sensor due to a pulse wave of the artery as the phase shift between the transmitted wave and the reflected wave, so that it may continuously detect the blood pressure based on this phase shift (radio wave irradiation method). Further, if a physical quantity capable of calculating blood pressure can be observed, a method other than these may be applied.

The above embodiment is an example, and various modifications can be made without departing from the scope of the present invention. The plurality of embodiments described above can be established independently, but combinations of the embodiments are also possible. Further, although various features in different embodiments can be established independently, it is also possible to combine features in different embodiments.

The invention claimed is:

1. A medical system that collects, processes and displays a correlation between blood pressure surge information and bodily state information of a subject which are obtained during a same predetermined sleep time period, the medical system comprising:

a tonometry type sphygmomanometer configured to repeatedly measure a time-series data of blood pressure of the subject during the predetermined sleep time period of the subject;

a bodily state sensor group configured to repeatedly measure and output the bodily state information of a bodily state of the subject during the predetermined sleep time period; and a processor programmed to:

detect one or more blood pressure surges during the predetermined sleep time period of the subject based on predetermined determination criteria for the time-series data of blood pressure that changes in conjunction with a pulsation of the subject, input the bodily state information repeatedly taken during the predetermined sleep time period of the subject indicating the bodily state of the subject including at least one of an apnea condition and a hypopnea condition, along with the time-series data of the blood pressure, extract from the time-series data of blood pressure obtained during the predetermined sleep time period of the subject, a feature value of each of the blood pressure surges including at least one of: a surge fluctuation amount during a rising time from a start of the blood pressure surge to a peak point of the blood pressure surge; a rising surge rate; a surge fluctuation amount during a falling time from the peak point of the blood pressure surge to an end of the blood pressure surge; a falling surge rate; a surge area in the rising time or in the falling time; and a surge time span including a time span of the rising time and a time span of the falling time, perform statistical processing of the extracted feature values of the blood pressure surges, the statistical processing including at least one of an average, a standard deviation, a maximum value, a minimum value, and a quartile, of a plurality of the feature values of the blood pressure surges, wherein the processor selectively performs the statistical processing of the extracted feature values that occur during a detected apnea or hypopnea event in within the predetermined sleep time period;

calculate a feature value of the bodily state of the subject from each input bodily state information obtained during the predetermined sleep time period of the subject, the feature value of the bodily state being at least one of: an apnea and hypopnea index measured per a predetermined time length; an average value of the apnea or hypopnea duration; an average value of a reduction amount of a percutaneous arterial oxygen saturation at a time of occurrence of the blood pressure surge; an average value of a reduction time of percutaneous arterial oxygen saturation; an average value of a bottom value of percutaneous arterial oxygen saturation; a variation average value of a heart rate or a pulse rate; an average value of a peak value of the heart rate or the pulse rate; and a statistical amount of a median, correlate, after each predetermined sleep time period, a numerical relationship between (i) the statistically processed feature values of the blood pressure surges and (ii) the calculated feature values of the bodily state obtained within the same predetermined sleep time period, and perform processing for displaying on a display screen, after each predetermined sleep time period, a correlation graph showing a series of correlations for different predetermined sleep time periods including a latest correlation result that is separately displayed from one or more correlation results obtained before the latest correlation result, wherein the processor is programmed to associate user-entered medication information with the latest correlation result, and perform a process of displaying an updated correlation graph to show the latest correlation result and the associated user-entered medication information.

2. The system according to claim 1, wherein the processor sets on the display screen a coordinate system in the correlation graph which is defined by a first axis representing the statistically processed feature values of the blood pressure surges and a second axis representing the calculated feature values of the bodily state.

3. A medical method that collects, processes and displays a correlation between blood pressure surge information and bodily state information of a subject which are obtained during a same predetermined sleep time period, the method comprising:

measuring repeatedly, by a tonometry type sphygmomanometer, a time-series data of blood pressure of the subject during the predetermined sleep time period of the subject;

measuring repeatedly and outputting, by a bodily state sensor group, the bodily state information of a bodily state of the subject during the predetermined sleep time period;

detecting, by a processor, one or more blood pressure surges during the predetermined sleep time period of the subject based on predetermined determination criteria for the time-series data of blood pressure that changes in conjunction with a pulsation of the subject;

inputting, by the processor, the bodily state information repeatedly taken during the predetermined sleep time period of the subject indicating the bodily state of the subject including at least one of an apnea condition, and a hypopnea condition, along with the time-series data of the blood pressures;

extracting, by the processor, from the time series data of blood pressure obtained during the predetermined sleep time period of the subject, a feature value of each of the blood pressure surges including at least one of: a surge fluctuation amount during a rising time from a start of the blood pressure surge to a peak point of the blood pressure surge; a rising surge rate; a surge fluctuation amount during a falling time from the peak point of the blood pressure surge to an end of the blood pressure surge; a falling surge rate; a surge area in the rising time or in the falling time; and a surge time span including a time span of the rising time and a time span of the falling time;

performing, by the processor, statistical processing of the extracted feature values of the blood pressure surges, the statistical processing including at least one of an average, a standard deviation, a maximum value, a minimum value, and a quartile, of a plurality of the feature values of the blood pressure surges, wherein the statistical processing includes selectively performing the statistical processing on the extracted feature values that occur during a detected apnea or hypopnea event in within the predetermined sleep time period;

calculating, by the processor, a feature value of a bodily state of the subject from each input bodily state information obtained during the predetermined sleep time period of the subject, the feature value of the bodily state being at least one of: an apnea and hypopnea index measured per a predetermined time length; an average value of the apnea or hypopnea duration; an average value of a reduction amount of a percutaneous arterial oxygen saturation at a time of occurrence of the blood pressure surge; an average value of a reduction time of percutaneous arterial oxygen saturation; an average value of a bottom value of percutaneous arterial oxygen saturation; a variation average value of a heart rate or a pulse rate; an average value of a peak value of the heart rate or the pulse rate; and a statistical amount of a median;

correlating, by the processor, after each predetermined sleep time period, a numerical relationship between (i) the statistically processed feature values of the blood pressure surges and (ii) the calculated feature values of the bodily state obtained within the same predetermined sleep time period;

performing processing, by the processor, for displaying on a display screen after each predetermined sleep time period, a correlation graph showing a series of correlations for different predetermined sleep time periods including a latest correlation result that is separately displayed from one or more correlation results obtained before the latest correlation result;

associating, by the processor, user-entered medication information with the latest correlation result; and performing, by the processor, a process of displaying an updated correlation graph to show the latest correlation result and the associated user-entered medication information.

4. A non-transitory computer-readable computer medium having instructions stored therein, which, when executed by a computer, cause the computer to perform the method of claim 3.

* * * * *